US006489302B1

(12) United States Patent
Wiessler et al.

(10) Patent No.: US 6,489,302 B1
(45) Date of Patent: Dec. 3, 2002

(54) SACCHARIDE CONJUGATES

(75) Inventors: Manfred Wiessler, Frankenthal (DE); Konrad Beyreuther, Heidelberg (DE)

(73) Assignee: Deutches Krebsforschungszentrum Stiftung Des Offentlichen Rechts, Heidelberg (DE)

( * ) Notice: Subject to any disclaimer, the term of this patent is extended or adjusted under 35 U.S.C. 154(b) by 0 days.

(21) Appl. No.: 08/981,672

(22) PCT Filed: Jul. 5, 1996

(86) PCT No.: PCT/DE96/01206

§ 371 (c)(1), (2), (4) Date: Apr. 20, 1998

(87) PCT Pub. No.: WO97/02046

PCT Pub. Date: Jan. 23, 1997

(30) Foreign Application Priority Data

Jul. 5, 1995 (DE) .......................................... 195 24 515

(51) Int. Cl.[7] ........................ A61K 31/70; A61K 31/715
(52) U.S. Cl. .............................. 514/25; 514/53; 514/54; 514/885; 514/904
(58) Field of Search ............................. 514/25, 53, 54, 514/885, 904

(56) References Cited

U.S. PATENT DOCUMENTS 4,337,760 A * 7/1982 Rubin
5,639,737 A * 6/1997 Rubin

FOREIGN PATENT DOCUMENTS

| DD | 122 386 A | 10/1976 |
|---|---|---|
| EP | 0 369 182 A | 5/1990 |
| EP | 0 526 649 A | 2/1993 |

OTHER PUBLICATIONS

Chem. Pharm. Bull. (1995), 43(6), 920–6 CODEN: CPBTAL; ISSN: 0009–2363, 1995, XP002030260 Fujita, Tomoyuki et al. "Inhibitory effect of perillosides A and C, and related monoterpene glucosides on aldose reductase and their structure–activity relationships".

Cancer Chemother. Pharmacol. (1995), 35 (5) 364–70 CODEN: CCPHDZ; ISSN: 0344–5704, 1995, XP002030261, Pohl, J. et al. "D–19575—a sugar–linked isophosphoarmide mustard derivative exploiting transmembrane glucose transport."

Phytochemistry (1992), 31(9), 3265–7 CODEN: PYTCAS; ISSN: 0031–9422, 1992, XP002030262, Fujita, Tomoyuki et al.: "Perilloside A, a monoterpene glucoside from *Perilla frutescens*".

Database WPI, Section Ch, Week 9518 Derwent Publications Ltd., London, G; AN 95–133680, XP002030267 & JP 07 048 264 A (Nippon Terpene Kagaku KK), Feb. 21, 1995.

Database WPI, Section Ch, Week 9419 Derwent Publications Ltd., London, G; AN 94–156560, XP002030268 & JP 06 100 453 A (Nippon Terpene Kagaku KK), Apr. 12, 1994.

Chemical Abstracts, vol. 81. No. 5, Aug. 5, 1974, Columbus, Ohio, US; abstract No. 25895, Ovrutskii, V.M.: "2, 3,4, 6–Tetraacetyl–.alpha.–D–gucosyl esters of N–aryl–N', N'–bits (2–chloroethyl)diamidophos phoric acid" & Zh. Obshch. Khim (1974), 44(4), 896–9 CODEN: ZOKHA4, 1974.

Chemical Abstracts, vol. 69. No. 19, Nov. 4, 1968, Columbus, Ohio, US; abstract No. 77679, Gudkova, I.P. et al. "Glycosyl phosphitesds and Glycos phosphonites" XP00030266 & Zh. Obshch. Khim. (1968), 38 (6), 1340–4 CODEN: ZOKHA4, 1968.

Journal of Controlled Release, Bd. 19, Nr. 1/03, 1.Marz 1992, Seiten 109–120, X000261546, Friend D.R. et al: "Drug Glycosides in Oral Colon–Specific Drug Delivery".

Nuclear Medicine and Biology, Bd. 13, Nr, 1986, Exeter GB, Awirwin 7–12, XP002030263, Paul, R. et al.: "Scintigraphy with [18F]2–Fluoro–2–Deoxy–D–Glucose of Cancer Patients".

Cancer Chemother. Pharmacol. (1996), 38 (4), 355–365 CODEN: CCPHDZ; ISSN: 0344–5704, 1996, XP002030264 Steuben, Joerg, et al."Pharmacokinetics and whole–body distribution of the new chemotherapeutic agent.beta.–D–glucosylisophosporamide mustards its effects on the incorporation of [methyl– 3H]–thymidine in various tissues of the rat".

* cited by examiner

*Primary Examiner*—James O. Wilson
(74) *Attorney, Agent, or Firm*—Burns, Doane, Swecker & Mathis, L.L.P.

(57) ABSTRACT

This invention relates to a conjugate, comprising a saccharide and one or more therapeutic or diagnostic agents, as well as the use of the conjugate. The conjugate of the present invention may be used for diagnosing cancer or viral diseases. The conjugate of the present invention may also be used to prevent and/or treat neurological diseases.

12 Claims, No Drawings

SACCHARIDE CONJUGATES

The present invention relates to saccharide conjugates and their use.

In general, many agents, particularly those serving for cancer treatment and those which shall reach certain organs and the cells thereof, e.g. brain, neurons, gliacytes, astrogliacytes and non-neuronal cells, are accompanied by the problem that they are poorly transported to their site of action and thus have considerable side-effects.

Therefore, it is the object of the present invention to provide a product by which agents of the most varying kinds can be transported in well-calculated fashion to their site of action, so that their side-effects can be reduced.

According to the invention this is achieved by the subject matters defined in the claims.

Thus, the subject matter of the present invention relates to a conjugate, comprising a saccharide and one or more agents.

The present invention is based upon the applicant's finding that β-D-glucose isophosphoramide has good antitumor properties and extremely low side-effects as compared to cyclophosphoramide and isophosphoramide. Furthermore, he has found that β-D-glucose isophosphoramide reaches the tumor cells by means of site-directed transport. For this transport, a glucose transporter has proved to be essential.

On the basis of the above findings, conjugates were developed which have one or more agents bonded to a saccharide, particularly a monosaccharide, disaccharide or oligosaccharide. Particularly glucose, more particularly D-glucose, galactose, mannose, arabinose, xylose, fucose, rhamnose, 2-amino-2-deoxyglucose, 2-fluoro-2-deoxyglucose, N-acetyl-2-amino-2-deoxyglucose, N-acetyl-2-amino-2-deoxy-galactose, digitoxose and 2-amino-2-deoxygalactose have to be mentioned as monosaccharide. Suitable disaccharides are particularly maltose, lactose or gentiobiose, either 1,4-linked or 1,6-linked. Particularly a linear and branched, e.g. di-, tri-, especially N,N'-di-2-chloroethyl-(3,6-di-O-(β-D-glucopyranosyl)-β-D-glucopyranosyl)-phosphoric ester diamide, and tetraantennary oligosaccharide have to be mentioned as oligosaccharide.

Every therapeutically and/or diagnostically usable substances are in consideration as agents. These are particularly: antioxidants, e.g. cysteine, N-acetylcysteine, α-tocopherol (vitamin E), probucol, α-lipoic acid, limonene (perillic acid), xanthines, carotenoids and nitrons, antirheumatics antiallergics, antianemic agents, antibiotics, e.g. sulfonamides, antidiabetics, antiemetics, antihistaminics, antiepileptics, β-receptor blockers, calcium antagonists, ACE inhibitors, bronchodilating agents, antiasthmatics, cholinergics, corticoids, dermatics, diuretics, enzyme inhibitors, remedies for gout, remedies for influenza, sedative agents, immunotherapeutic agents, hepato-therapeutic agents, antilipemics, remedies for migraine, muscle relaxants, anesthetics, neuropathy preparations, antihyperkinetic agents, psychoactive drugs, thyreotherapeutic agents, sex hormones and their inhibitors, antispasmodic agents, vitamins, wound treating agents, analgesics, e.g. indomethacin, paracetamol, ibuprofen and acetylsalicylic acid, cimetidine, oncotherapeutic agents, e.g. cyclophosphoramide, isophosphoramide, cisplatin complexes, antimetabolites, such as methotrexate and 5-fluorouracil deoxyribonucleoside, and topoisomerase inhibitors such as mitoxanthrone, tumor diagnostic agents, radiosensitizers, e.g. misonidazole, inhibitors of DNA repair, e.g. $O^6$-benzyldeoxyguanosine, α-sympathicomimetics, e.g. L-dopa and dopamine, nucleic acids, e.g. oligonucleotides, and anti-AIDS agents, such as azidothymidine, dideoxyinositol and dideoxycytidine.

The linkage between the saccharide and the agent or agents may be present as usual. It is favorable when there is at least a linkage via the 1-position of the saccharide. This includes the advantage that at the site of action, i.e. in the cell, the agent linked via the 1-position of the saccharide is cleaved enzymatically and released.

In a preferred embodiment of the conjugate according to the invention, the saccharide is linked at least with one agent via a common linker. Suitable linkers are particularly diols, more particularly short-chain diols from 1,2-diol, e.g. ethylene glycol, to 1,6-hexanediol.

Conjugates according to the invention accumulate in cells, organs and tissues which have glucose transporters and/or related transporters thereof. The conjugates accumulate particularly in the liver, kidney, heart, thymus, thyroid gland, intestines, and brain as well as in all kinds of tumors.

Therefore, conjugates according to the invention are especially suitable for treating neurologic diseases, such as Alzheimer's disease, apoplexy, Parkinson's disease and other dementia diseases. For this purpose, it is favorable when the conjugates contain antioxidants as agent. These agents prevent that in aerobic cells an incomplete reaction of oxygen takes place in the mitochondrial electron-transport chain and thus superoxide radicals, hydroxyl peroxides or hydroxyl radicals being released into the cytosol, which may cause apoptosis. In the case of apoplexy and other arteriosclerotic diseases, especially the oxidation of LDL particles into lipid peroxides, which represent a critical occurrence with the formation of arteriosclerotic plaques, is inhibited by the administration of andioxidants. When Parkinson's disease is treated, the use of L-dopa or dopamine as agent has also proved its value.

Conjugates according to the invention, which contain antioxidants as agents, are also suitable for treating cardiovascular diseases, diabetes, inflammations, particularly rheumatic arthritis, inflammatory intestinal diseases and pancreatitis, high-blood pressure and pulmonary diseases, e.g. idiopathic pulmonary fibrosis and cystic fibrosis, AIDS-caused apoptosis of CD4-T cells, arteriosclerosis, osteoporosis, ischemia, cataract as well as multiple sclerosis. Furthermore, such conjugates are also suited for the prevention of the above-mentioned diseases, particularly arteriosclerotic diseases and Alzheimer's disease.

In addition, when they contain corresponding agents, conjugates according to the invention can be used successfully for treating and/or diagnosing tumors. Examples of therapeutically usable agents are cyclo-phosphoramide and isophosphoramide. Furthermore, particularly radiosensitizers such as misonidazole have to be mentioned which result in a tumor-specific enhancement of a radiotherapy and/or photodynamic treatment. Moreover, particularly inhibitors of DNA repair such as $O^6$ benzyl deoxyguanosine have to be mentioned. These agents contribute to the tumor-specific reduction of the DNA repair capacity and thus to the improvement of a treatment by alkylating tumor-chemotherapeutic agents. Conjugates containing antioxidants are also suitable for tumor treatment and the prevention of tumor diseases. As explained above, these agents serve for stopping the formation of free radicals which are known to result in cellular injury and promote degeneration of cells. Thus, conjugates having antioxidants may also be used for protecting healthy cells in the case of chemotherapies and radiation therapies. In addition, the most recent applicant's results refer to the fact that when inventive conjugates containing oncotherapeutic agents are administered, much less resistance is developed than upon administration of oncotherapeutic agents alone.

Moreover, conjugates according to the invention, which contain nucleic acids, e.g. oligonucleotides, as agents, are suitable for diagnosis and/or treatment of genetic defects, particularly those which are organ-specific.

Besides, conjugates according to the invention can also be used for controlling pathogens of any kind, which have a glucose transporter or a transporter related thereto. Such pathogens are especially viruses, bacteria and protozoan organisms. Thus, conjugates according to the invention are also suited for treating diseases caused by such pathogens, e.g. viral infections, particularly AIDS.

The invention is explained by the below examples.

EXAMPLE 1

Preparation of a Conjugate According to the Invention, β-D-Galactopyranoside-[4-(1-methylethenyl)-1-cyclohexene-1-yl]methyl 250 ml of absolute diethyl ether, 7.5 g of silver carbonate, 25 g of finely pulverized molecular sieve (4 Å) and 2.3 ml (0.15 mole) of the antioxidant S(-)perilla alcohol were stirred in a baked 500 ml three-neck flask with protection from light for 15 min. Then, 6 g (0.15 mole) of tetraacetyl-α-bromogalactose were added to 100 ml absolute diethyl ether in small portions for one hour. The reaction was observed by thin-layer chromatography (silica gel PE/acetic ester 4:1 v/v). The reaction mixture was filtered after 10 hours and the solid residues were washed with acetone. The residues were then washed with 5 % $NaHCO_3$ solution and water, dried with $Na_2SO_4$, concentrated in vacuo and purified by means of column chromatography (silica gel PE/acetic ester 6:1 v/v). 3.05 g of the anomer mixture were obtained as colorless oil. HPLC chromatography showed a product ratio of β:α=2.92 . The acetyl protective groups were separated in almost quantitative yield by conversion with triethylamine at room temperature for 1 hour.

The resulting product has the structural formula:

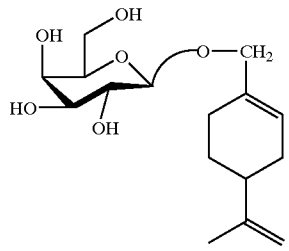

EXAMPLE 2

Preparation and use of a Conjugate According to the Invention, β-D-Glucosylisophosphoramide (β-D-Glc-IPM)

1.0 mM of glycosylimidate was dissolved in 20 ml of acetonitrile. Having added 1.0 mM of isophosphoramide (Haloxan$^R$), the mixture was refluxed in the dark for 6 hours. Following filtration and concentration by rotation, chromatography was carried out with silica gel according to common methods. The resulting β-D-Glc-IMP has the following structural formula:

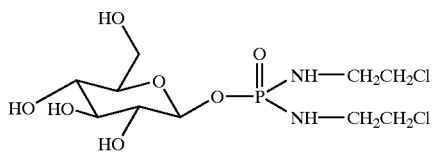

This conjugate was labeled with $^{14}C$ according to common methods and used for the following treatment of rats.

The rats used were female Sprague-Dawley rats (SD rats; obtainable from Charles River Wiga, Sulzfeld, Germany) and male Copenhagen rats (obtainable from Harlan Sprague Dawley, Ind., U.S.A.).

Fresh pieces (2×2 mm) of Dunning prostate tumor tissue were transplanted into the Copenhagen rats. The tumors were allowed to grow for about one week until they were well palpable but not yet necrotic.

Groups of 5 healthy SD rats were given i.v. injections of 315 mg/kg β-D-Glc-IMP and 56.2 mg/kg of β-D-Glc-IMP, respectively. 5 of the tumor-bearing Copenhagen rats were given 315 mg/kg of β-D-Glc-IMP. The radioactive dose per injection was about 20 µCi. One animal of every group was killed with $CO_2$ 10 minutes, 1 hours, 2 hours, 8 hours and 24 hours, respectively, after the administration of the injection. The tissues of the rats were prepared for a common microtome preparation and the sections were subjected to autoradiography as described by Ullberg, S., (1977), in: Alvefeldt, O. (ed.) Special issue on whole-body autoradiography. Science Tools, Bromma, Sweden, p. 2).

It showed that the conjugate according to the invention had accumulated in organs, particularly the liver, kidneys, thymus and thyroid gland, after only 10 minutes. Central nervous system, including the brain, contained the conjugate after 8 hours. Moreover, a strong accumulation of the conjugate was also found in tumor tissue.

What is claimed is:

1. A method for the treatment of tumor disease, said method comprising administering to a patient a conjugate comprising an agent selected from the group consisting of cyclophosphoramide, isophosphoramide, cisplatin complexes, antimetabolites, topoisomerase inhibitors, antioxidants, radiosensitizers, inhibitors of DNA repair, nucleic acids and AIDS agents; linked with a saccharide selected from the group consisting of glucose, D-glucose, galactose, mannose, arabinose, xylose, fucose, rhamnose, 2-amino-2-deoxyglucose, 2-fluoro-2-deoxyflucose, N-acetyl-2-amino-2-deoxyglucose, N-acetyl-2-amino-2-deoxygalactose, digitoxose, 2-amino-2-deoxygalactose, maltose, gentiobiose, N,N'-di-2-chloroethyl-(3,6-di-O-(β-D-glucopyranosyl)-β-D-glucopyranosyl)-phosphoric ester diamide, and tetraantennary oligosaccharides, wherein said conjugates are uptaken by a transporter into cells.

2. The method of claim 1, wherein said antioxidant is selected from the group consisting of cysteine, N-acetylcysteine, α-tocopherol (vitamin E), probucol, α-lipoic acid, limonene (perillic acid), xanthines, carotinoids, and nitrones and mixtures thereof.

3. The method of claim 1, wherein said radiosensitizer is misonidazole.

4. The method of claim 1, wherein said inhibitor of the DNA repair is $O^6$-benzyl deoxyguanosine.

5. The method of claim 1, wherein said anti-AIDS agent is selected from the group consisting of azidothymidine, dideoxyinositol and dideoxycytidine and mixtures thereof.

6. The method as defined by claim 1, wherein said agent is linked to said saccharide via the 1-position of said saccharide.

7. The method as defined by claim 1, wherein said saccharide is a monosaccharide.

8. The method as defined by claim 7, wherein said monosaccharide is selected from the group consisting of glucose, galactose, mannose, arabinose, xylose, fucose, rhamnose, 2-amino-2-deoxyglucose, 2-fluoro-2-deoxyglucose, N-acetyl-2-amino-2-deoxyglucose, N-acetyl-2-amino-2-deoxygalactose, 2-amino-2-deoxygalactose, digitoxose and mixtures thereof.

9. The method as defined by claim 1, wherein said saccharide is a disaccharide.

10. The method as defined by claim 9, wherein said disaccharide is selected from the group consisting of maltose, lactose, gentiobiose and mixtures thereof.

11. The method as defined by claim 1, wherein said saccharide is linked via a linker to said agent.

12. The method as defined by claim 11, wherein said linker is a short chain diol.

* * * * *

UNITED STATES PATENT AND TRADEMARK OFFICE
CERTIFICATE OF CORRECTION

PATENT NO. : 6,489,302 B1
DATED : December 3, 2002
INVENTOR(S) : Manfred Wiessler and Konrad Beyreuther It is certified that error appears in the above-identified patent and that said Letters Patent is hereby corrected as shown below:

Column 1, line 44 through Column 2, line 6,
Correct to read:
-- Every therapeutically and/or diagnostically usable substances are in consideration as agents. These are particularly:
antioxidants, e.g. cysteine, N-acetylcysteine, α-tocopherol (vitamin E), probucol, α-lipoic acid, limonene (perillic acid), xanthines, carotenoids and nitrons, antirheumatics antiallergics, antianemic agents, antibiotics, e.g. sulfonamides, antidiabetics, antiemetics, antihistaminics, antiepileptics, β-receptor blockers, calcium antagonists, ACE inhibitors, bronchodilating agents, antiasthmatics, cholinergics, corticoids, dermatics, diuretics, enzyme inhibitors, remedies for gout, remedies for influenza, sedative agents, immunotherapeutic agents, hepato-therapeutic agents, antilipemics, remedies for migraine, muscle relaxants, anesthetics, neuropathy preparations, antihyperkinetic agents, psychoactive drugs, thyreo-therapeutic agents, sex hormones and their inhibitors, antispasmodic agents, vitamins, wound treating agents, analgesics, e.g. indomethacin, paracetamol, ibuprofen and acetylsalicylic acid, cimetidine, oncotherapeutic agents, cisplatin complexes, antimetabolites, such as methotrexate and 5-fluorouracil deoxyribonucleoside, and topoisomerase inhibitors such as mitoxanthrone, tumor diagnostic agents, radiosensitizers, e.g. misonidazole, inhibitors of DNA repair, e.g. $O^6$-benzyldeoxyguanosine, α-sympathicomimetics, e.g. L-dopa and dopamine, nucleic acids, e.g. oligonucleotides, and anti-AIDS agents, such as azidothymidine, dideoxyinositol and dideoxycytidine. --

Column 2, line 50 through Column 3, line 6,
Please correct to read:
-- In addition, when they contain corresponding agents, conjugates according to the invention can be used successfully for treating and/or diagnosing tumors. Furthermore, particularly radiosensitizers such as misonidazole have to be mentioned which result in a tumor-specific enhancement of a radiotherapy and/or photodynamic treatment. Moreover, particularly inhibitors of DNA repair such as $O^6$ benzyl deoxyguanosine have to be mentioned. These agents contribute to the tumor-specific reduction of the DNA repair capacity and thus to the improvement of a treatment by alkylating tumor-chemotherapeutic agents. Conjugates containing antioxidants are also suitable for tumor treatment and the prevention of tumor diseases. As explained above, these agents serve for stopping the formation of free radicals which are known to result in cellular injury and promote degeneration of cells. Thus, conjugates having antioxidants may also be used for protecting healthy cells in the case of chemotherapies and radiation thera pies. In addition, the most recent applicant's results refer to the fact that when inventive conjugates containing oncotherapeutic agents are administered, much less resistance is developed than upon administration of oncotherapeutic agents alone. --

UNITED STATES PATENT AND TRADEMARK OFFICE
CERTIFICATE OF CORRECTION

PATENT NO. : 6,489,302 B1
DATED : December 3, 2002
INVENTOR(S) : Manfred Wiessler and Konrad Beyreuther It is certified that error appears in the above-identified patent and that said Letters Patent is hereby corrected as shown below:

Column 4,
Lines 40-45, please correct Claim 1 as follows:
-- 1. A method for the treatment of tumor disease, said method comprising administering to a patient a conjugate comprising an agent selected from the group consisting of cisplatin complexes, antimetabolites, topoisomerase inhibitors, antioxidants, radiosensitizers, inhibitors of DNA repair, nucleic acids and AIDS agents; linked with a saccharide selected from the group consisting of glucose, D-glucose, galactose, mannose, arabinose, xylose, fucose, rhamnose, 2-amino-2-deoxyglucose, 2-fluoro-2-deoxyflucose, N-acetyl-2-amino-2-deoxyglucose, N-acetyl-2-amino-2-deoxygalactose, digitoxose, 2-amino-2-deoxygalactose, maltose, gentiobiose, N,N'-di-2-chloroethyl-(3,6-di-O-(β-D-glucopyranosyl)-β-D-glucopy ranosyl)-phosphoric ester diamide, and tetraantennary oligosaccharides, wherein said conjugates are uptaken by a transporter into cells. --

Signed and Sealed this

Fourth Day of November, 2003

JAMES E. ROGAN
*Director of the United States Patent and Trademark Office*